(12) United States Patent
Carman

(10) Patent No.: US 11,889,869 B2
(45) Date of Patent: Feb. 6, 2024

(54) CLOSED-LOOP CONTROL OF TEMPERATURE AND PRESSURE SENSING FOR AN AEROSOL PROVISION DEVICE

(71) Applicant: RAI Strategic Holdings, Inc., Winston-Salem, NC (US)

(72) Inventor: Sky Carman, Clemmons, NC (US)

(73) Assignee: RAI Strategic Holdings, Inc., Winston-Salem, NC (US)

( * ) Notice: Subject to any disclaimer, the term of this patent is extended or adjusted under 35 U.S.C. 154(b) by 590 days.

(21) Appl. No.: 17/099,178

(22) Filed: Nov. 16, 2020

(65) Prior Publication Data
US 2022/0151303 A1    May 19, 2022

(51) Int. Cl.
  *A24F 40/51* (2020.01)
  *A24F 40/57* (2020.01)
  *A24F 40/42* (2020.01)
  *G05B 19/18* (2006.01)
  *A61M 15/06* (2006.01)

(52) U.S. Cl.
  CPC .............. *A24F 40/51* (2020.01); *A24F 40/42* (2020.01); *A24F 40/57* (2020.01); *G05B 19/18* (2013.01); *A61M 15/06* (2013.01); *G05B 2219/42033* (2013.01)

(58) Field of Classification Search
  CPC ....................................................... A24F 40/51
  See application file for complete search history.

(56) References Cited

U.S. PATENT DOCUMENTS

| | | | |
|---|---|---|---|
| 2,057,353 | A | 10/1936 | Whittemore, Jr. |
| 2,104,266 | A | 1/1938 | McCormick |
| 3,200,819 | A | 8/1965 | Gilbert |
| 4,922,901 | A | 5/1990 | Brooks et al. |
| 5,060,671 | A | 10/1991 | Counts et al. |
| 5,093,894 | A | 3/1992 | Deevi et al. |

(Continued)

FOREIGN PATENT DOCUMENTS

| CN | 1541577 A | 11/2004 |
|---|---|---|
| CN | 2719043 Y | 8/2005 |

(Continued)

*Primary Examiner* — Cynthia Szewczyk
(74) *Attorney, Agent, or Firm* — Womble Bond Dickinson (US) LLP

(57) ABSTRACT

An aerosol provision device includes a housing; circuitry; and a coupler or a receptacle structured to engage and hold a consumable including aerosol-generating material. The aerosol provision device or the consumable includes an aerosol generator powered to energize the aerosol-generating material. The circuitry includes a pressure sensor and a temperature sensor. The circuitry also includes a high-side load switch coupled to or coupleable with the aerosol generator, and processing circuitry coupled to the high-side load switch, the pressure sensor, and the temperature sensor. The processing circuitry is configured to output a modulated signal with an adjustable duty cycle to cause the high-side load switch to connect and disconnect power to the aerosol generator based on the measurements of pressure and temperature. The processing circuitry is configured to implement a proportional-integral-derivative (PID) algorithm to adjust the duty cycle based on pressure and temperature according to a predetermined relationship.

16 Claims, 10 Drawing Sheets

(56) References Cited

U.S. PATENT DOCUMENTS

| | | |
|---|---|---|
| 5,261,424 A | 11/1993 | Sprinkel, Jr. |
| 5,388,574 A | 2/1995 | Ingebrethsen et al. |
| 5,530,225 A | 6/1996 | Hajaligol |
| 5,687,746 A | 11/1997 | Rose et al. |
| 5,726,421 A | 3/1998 | Fleischhauer et al. |
| 5,865,185 A | 2/1999 | Collins et al. |
| 5,894,841 A | 4/1999 | Voges |
| 6,125,853 A | 10/2000 | Susa et al. |
| 6,155,268 A | 12/2000 | Takeuchi |
| 7,117,867 B2 | 10/2006 | Cox et al. |
| 7,832,410 B2 | 11/2010 | Hon |
| 8,314,591 B2 | 11/2012 | Terry et al. |
| 8,365,742 B2 | 2/2013 | Hon |
| 8,499,766 B1 | 8/2013 | Newton |
| 9,498,000 B2 | 11/2016 | Kuczaj |
| 2005/0016550 A1 | 1/2005 | Katase |
| 2006/0196518 A1 | 9/2006 | Hon |
| 2008/0092912 A1 | 4/2008 | Robinson et al. |
| 2009/0095311 A1 | 4/2009 | Hon |
| 2009/0126745 A1 | 5/2009 | Hon |
| 2009/0188490 A1 | 7/2009 | Hon |
| 2009/0272379 A1 | 11/2009 | Thorens et al. |
| 2011/0094523 A1 | 4/2011 | Thorens et al. |
| 2011/0126848 A1 | 6/2011 | Zuber et al. |
| 2011/0155718 A1 | 6/2011 | Greim et al. |
| 2011/0168194 A1 | 7/2011 | Hon |
| 2011/0265806 A1 | 11/2011 | Alarcon et al. |
| 2011/0290248 A1 | 12/2011 | Schennum |
| 2012/0111347 A1 | 5/2012 | Hon |
| 2012/0260927 A1 | 10/2012 | Liu |
| 2012/0279512 A1 | 11/2012 | Hon |
| 2013/0037041 A1 | 2/2013 | Worm et al. |
| 2013/0056013 A1 | 3/2013 | Terry et al. |
| 2013/0306084 A1 | 11/2013 | Flick |
| 2014/0000638 A1 | 1/2014 | Sebastian et al. |
| 2014/0060554 A1 | 3/2014 | Collett et al. |
| 2014/0060555 A1 | 3/2014 | Chang et al. |
| 2014/0096781 A1 | 4/2014 | Sears et al. |
| 2014/0096782 A1 | 4/2014 | Ampolini et al. |
| 2014/0209105 A1 | 7/2014 | Sears et al. |
| 2014/0253144 A1 | 9/2014 | Novak et al. |
| 2014/0261408 A1 | 9/2014 | DePiano et al. |
| 2014/0261486 A1 | 9/2014 | Potter et al. |
| 2014/0261487 A1 | 9/2014 | Chapman et al. |
| 2014/0261495 A1 | 9/2014 | Novak et al. |
| 2014/0270727 A1 | 9/2014 | Ampolini et al. |
| 2014/0270729 A1 | 9/2014 | DePiano et al. |
| 2014/0270730 A1 | 9/2014 | DePiano et al. |
| 2018/0043114 A1 | 2/2018 | Bowen et al. |
| 2019/0069599 A1 | 3/2019 | Monsees et al. |
| 2019/0387795 A1* | 12/2019 | Fisher ................... A24F 40/53 |
| 2020/0154788 A1 | 5/2020 | Novak, III et al. |
| 2021/0401061 A1* | 12/2021 | Davis ................... A24F 40/57 |

FOREIGN PATENT DOCUMENTS

| | | |
|---|---|---|
| CN | 201379072 Y | 1/2010 |
| CN | 111436672 | 7/2020 |
| EP | 0 295 122 A2 | 12/1988 |
| EP | 0 845 220 A1 | 6/1998 |
| EP | 1 618 803 A1 | 1/2006 |
| GB | 2469850 A | 11/2010 |
| WO | 2003/034847 A1 | 5/2003 |
| WO | 2004/080216 A1 | 9/2004 |
| WO | 2005/099494 A1 | 10/2005 |
| WO | 2007/131449 A1 | 11/2007 |

* cited by examiner

1000

START
↓
1002 — PRODUCE MEASUREMENTS OF PRESSURE
↓
1004 — PRODUCE MEASUREMENTS OF TEMPERATURE
↓
1006 — OUTPUT A SIGNAL TO CAUSE A SWITCH TO SWITCHABLY CONNECT AND DISCONNECT POWER FROM THE POWER SOURCE TO THE AEROSOL GENERATOR
↓
1008 — IMPLEMENT A PID ALGORITHM TO ADJUST THE DUTY CYCLE OF THE SIGNAL BASED ON THE MEASUREMENTS OF PRESSURE AND TEMPERATURE
↓
STOP

1010 — OUTPUT THE SIGNAL TO POWER THE AEROSOL GENERATOR FOR AN AEROSOL-PRODUCTION TIME PERIOD COEXTENSIVE WITH A PUFF ACTION

1012 — IMPLEMENT THE PID ALGORITHM WHEN THE MEASUREMENTS OF TEMPERATURE ARE BELOW OR ABOVE A TEMPERATURE TARGET THAT VARIES WITH THE MEASUREMENTS OF PRESSURE ACCORDING TO THE PREDETERMINED RELATIONSHIP

1014 — CAUSE THE REDUCTION OF A HYSTERESIS CONDITION AS THE DUTY CYCLE IS ADJUSTED TO REACH THE TEMPERATURE TARGET

FIG. 10C

CLOSED-LOOP CONTROL OF TEMPERATURE AND PRESSURE SENSING FOR AN AEROSOL PROVISION DEVICE

TECHNOLOGICAL FIELD

The present disclosure relates to aerosol provision systems such as smoking articles designed to deliver at least one substance to a user.

BACKGROUND

Many aerosol provision systems and in particular non-combustible aerosol provision systems have been proposed through the years as improvements upon, or alternatives to, smoking products that require combusting tobacco for use. These systems are generally designed to deliver at least one substance to a user, such as to satisfy a particular "consumer moment." To this end, the substance may include constituents that impart a physiological effect on the user, a sensorial effect on the user, or both. The substance may be generally present in an aerosol-generating material that may contain one or more constituents of a range of constituents, such as active substances, flavors, aerosol-former materials and other functional materials like fillers.

Aerosol provision systems include, for example, vapor products commonly known as "electronic cigarettes," "e-cigarettes" or electronic nicotine delivery systems (ENDS), as well as heat-not-burn products including tobacco heating products (THPs) and carbon-tipped tobacco heating products (CTHPs). Many of these products take the form of a system including a device and a consumable, and it is the consumable that includes the material from which the substance to be delivered originates. Typically, the device is reusable, and the consumable is single-use (although some consumables are refillable). Therefore, in many cases, the consumable is sold separately from the device, and often in a multipack. Moreover, subsystems and some individual components of devices or consumables may be sourced from specialist manufacturers.

BRIEF SUMMARY

Example implementations of the present disclosure are directed to closed loop control of temperature and pressure sensing for an aerosol provision device. This may be accomplished by monitoring temperature and/or pressure values and controlling power to an aerosol generator of the aerosol provision device. Such control may adjust the power to the aerosol generator based on actual, real-time usage of the device and may include the use of electronically controlled closed-loop feedback.

Such control may have the advantage of extending the life of the aerosol generator (e.g., reducing carbonization from overheating). Advantages may also include reducing the overheating of aerosol-generating material, therefore resulting in reducing or eliminating unwanted chemicals and/or tastes associated with overheating of the aerosol-generating material and the aerosol generator. Consumer value results from extending the life of the aerosol generator, and additional value is achieved in the form of consistent flavor delivery based on an individual's usage in the form of power control associated with temperature and pressure.

The present disclosure includes, without limitation, the following example implementations.

Some example implementations provide an aerosol provision device comprising: a housing; circuitry; and one or more of a coupler or a receptacle structured to engage and hold a consumable including aerosol-generating material, the aerosol provision device or the consumable further including an aerosol generator powered by a power source under control of the circuitry to energize the aerosol-generating material to generate an aerosol for delivery to a user, wherein the circuitry includes: a pressure sensor configured to produce measurements of pressure caused by airflow through the housing; a temperature sensor configured to produce measurements of temperature of one or both of the aerosol generator or the aerosol-generating material; a high-side load switch coupled to or coupleable with the aerosol generator; and processing circuitry coupled to the high-side load switch, the pressure sensor, and the temperature sensor, the processing circuitry configured to output a signal to cause the high-side load switch to switchably connect and disconnect power from the power source to the aerosol generator, based on the measurements of pressure and the measurements of temperature, wherein the signal is a modulated signal with a duty cycle that is adjustable, and the processing circuitry is configured to implement a proportional-integral-derivative (PID) algorithm to adjust the duty cycle based on the measurements of pressure and the measurements of temperature according to a predetermined relationship between pressure and temperature.

In some example implementations of the aerosol provision device of any preceding example implementation, or any combination of any preceding example implementations, the aerosol provision device further comprises the power source, and the high-side load switch is coupled to and between the power source and the aerosol generator.

In some example implementations of the aerosol provision device of any preceding example implementation, or any combination of any preceding example implementations, the processing circuitry is configured to implement the PID algorithm to adjust the duty cycle when the measurements of temperature are below or above a temperature target that varies with the measurements of pressure according to the predetermined relationship between pressure and temperature.

In some example implementations of the aerosol provision device of any preceding example implementation, or any combination of any preceding example implementations, the processing circuitry configured to implement the PID algorithm to adjust the duty cycle when the measurements of temperature are below or above the temperature target causes the reduction of a hysteresis condition in one or both of the aerosol generator or the aerosol-generating material as the duty cycle is adjusted to reach the temperature target.

In some example implementations of the aerosol provision device of any preceding example implementation, or any combination of any preceding example implementations, the measurements of temperature include initial measurements of temperature produced after an initial puff action in which the initial measurements of temperature are below an initial temperature target that is less than the temperature target, and the processing circuitry is configured to output the signal with a longer duty cycle to pre-heat the aerosol-generating material or the aerosol generator to the initial temperature target.

In some example implementations of the aerosol provision device of any preceding example implementation, or any combination of any preceding example implementations, the modulated signal is a pulse-width modulation (PWM) signal or a pulse-frequency modulation (PFM) signal.

In some example implementations of the aerosol provision device of any preceding example implementation, or any combination of any preceding example implementations, the temperature sensor is a resistance temperature detector (RTD).

In some example implementations of the aerosol provision device of any preceding example implementation, or any combination of any preceding example implementations, the processing circuitry configured to output the signal includes the processing circuitry configured to output the signal to power the aerosol generator for an aerosol-production time period that is coextensive with a puff action.

In some example implementations of the aerosol provision device of any preceding example implementation, or any combination of any preceding example implementations, the predetermined relationship is one in which the measurements of temperature or the measurements of pressure are determined by the processing circuitry to take precedence for implementing the PID algorithm to adjust the duty cycle.

Some example implementations provide a method of operating an aerosol provision system equipped with circuitry including processing circuitry, and an aerosol generator powered by a power source under control of the circuitry to energize aerosol-generating material to generate an aerosol for delivery to a user, the method comprising: producing measurements of pressure caused by airflow through the aerosol provision device; producing measurements of temperature of one or both of the aerosol generator or the aerosol-generating material; and outputting a signal by the processing circuitry to cause a high-side load switch to switchably connect and disconnect power from the power source to the aerosol generator, based on the measurements of pressure and the measurements of temperature, wherein the signal output by the processing circuitry is a modulated signal with a duty cycle that is adjustable, the processing circuitry implementing a proportional-integral-derivative (PID) algorithm to adjust the duty cycle based on the measurements of pressure and the measurements of temperature according to a predetermined relationship between pressure and temperature.

In some example implementations of the method of any preceding example implementation, or any combination of any preceding example implementations, the aerosol provision device is further equipped with the power source, and the high-side load switch is coupled to and between the power source and the aerosol generator.

In some example implementations of the method of any preceding example implementation, or any combination of any preceding example implementations, the processing circuitry implements the PID algorithm to adjust the duty cycle when the measurements of temperature are below or above a temperature target that varies with the measurements of pressure according to the predetermined relationship between pressure and temperature.

In some example implementations of the method of any preceding example implementation, or any combination of any preceding example implementations, the processing circuitry implements the PID algorithm to adjust the duty cycle when the measurements of temperature are below or above the temperature target to cause the reduction of a hysteresis condition in one or both of the aerosol generator or the aerosol-generating material as the duty cycle is adjusted to reach the temperature target.

In some example implementations of the method of any preceding example implementation, or any combination of any preceding example implementations, the measurements of temperature include initial measurements of temperature produced after an initial puff action in which the initial measurements of temperature are below an initial temperature target that is less than the temperature target, and the signal output by the processing circuitry includes a longer duty cycle to pre-heat the aerosol-generating material or the aerosol generator to the initial temperature target.

In some example implementations of the method of any preceding example implementation, or any combination of any preceding example implementations, the modulated signal is a pulse-width modulation (PWM) signal or a pulse-frequency modulation (PFM) signal.

In some example implementations of the method of any preceding example implementation, or any combination of any preceding example implementations, the temperature sensor is a resistance temperature detector (RTD).

In some example implementations of the method of any preceding example implementation, or any combination of any preceding example implementations, outputting the signal includes outputting the signal to power the aerosol generator for an aerosol-production time period that is coextensive with a puff action.

In some example implementations of the method of any preceding example implementation, or any combination of any preceding example implementations, the predetermined relationship is one in which the measurements of temperature or the measurements of pressure are determined by the processing circuitry to take precedence for implementing the PID algorithm to adjust the duty cycle.

These and other features, aspects, and advantages of the present disclosure will be apparent from a reading of the following detailed description together with the accompanying figures, which are briefly described below. The present disclosure includes any combination of two, three, four or more features or elements set forth in this disclosure, regardless of whether such features or elements are expressly combined or otherwise recited in a specific example implementation described herein. This disclosure is intended to be read holistically such that any separable features or elements of the disclosure, in any of its aspects and example implementations, should be viewed as combinable, unless the context of the disclosure clearly dictates otherwise.

It will therefore be appreciated that this Brief Summary is provided merely for purposes of summarizing some example implementations so as to provide a basic understanding of some aspects of the disclosure. Accordingly, it will be appreciated that the above described example implementations are merely examples and should not be construed to narrow the scope or spirit of the disclosure in any way. Other example implementations, aspects and advantages will become apparent from the following detailed description taken in conjunction with the accompanying figures which illustrate, by way of example, the principles of some described example implementations.

BRIEF DESCRIPTION OF THE FIGURES

Figure 1:
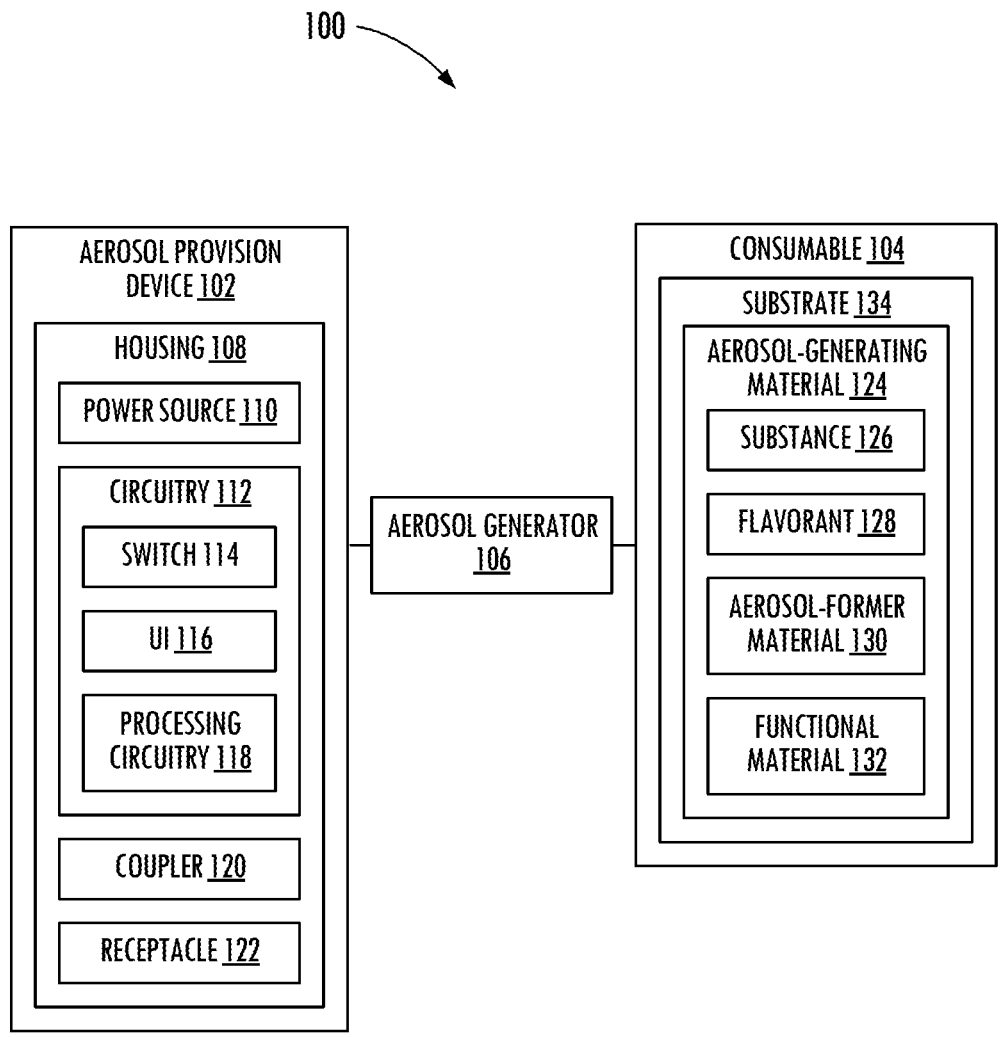
Figure 2:
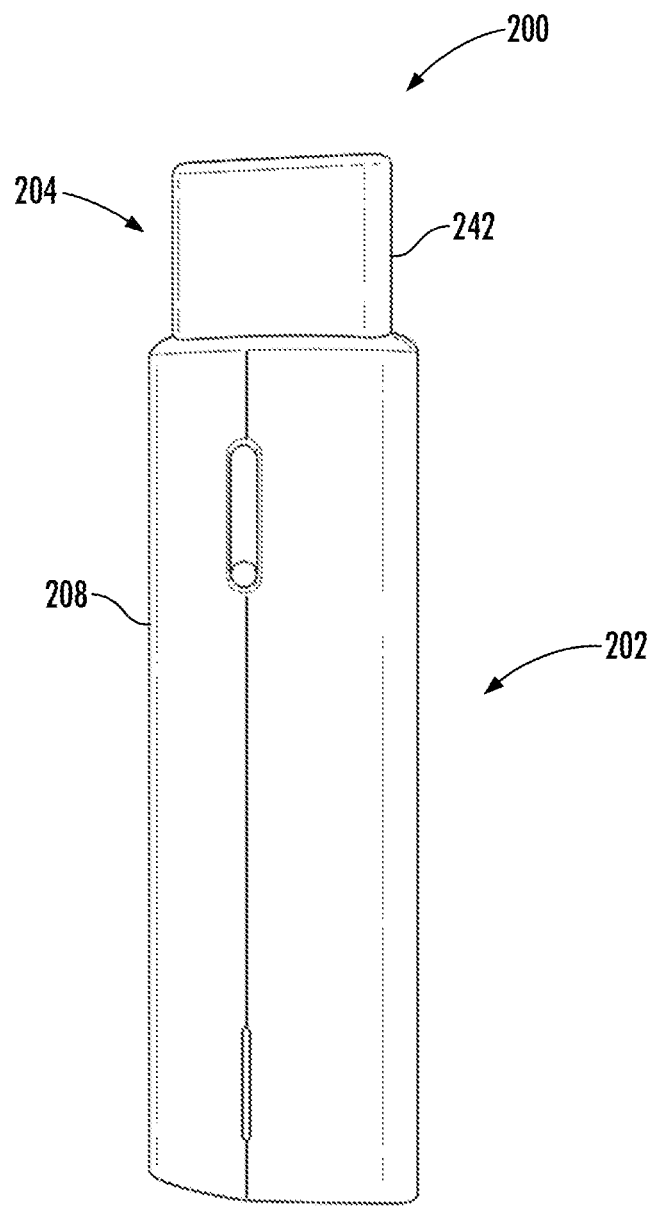
Figure 3:
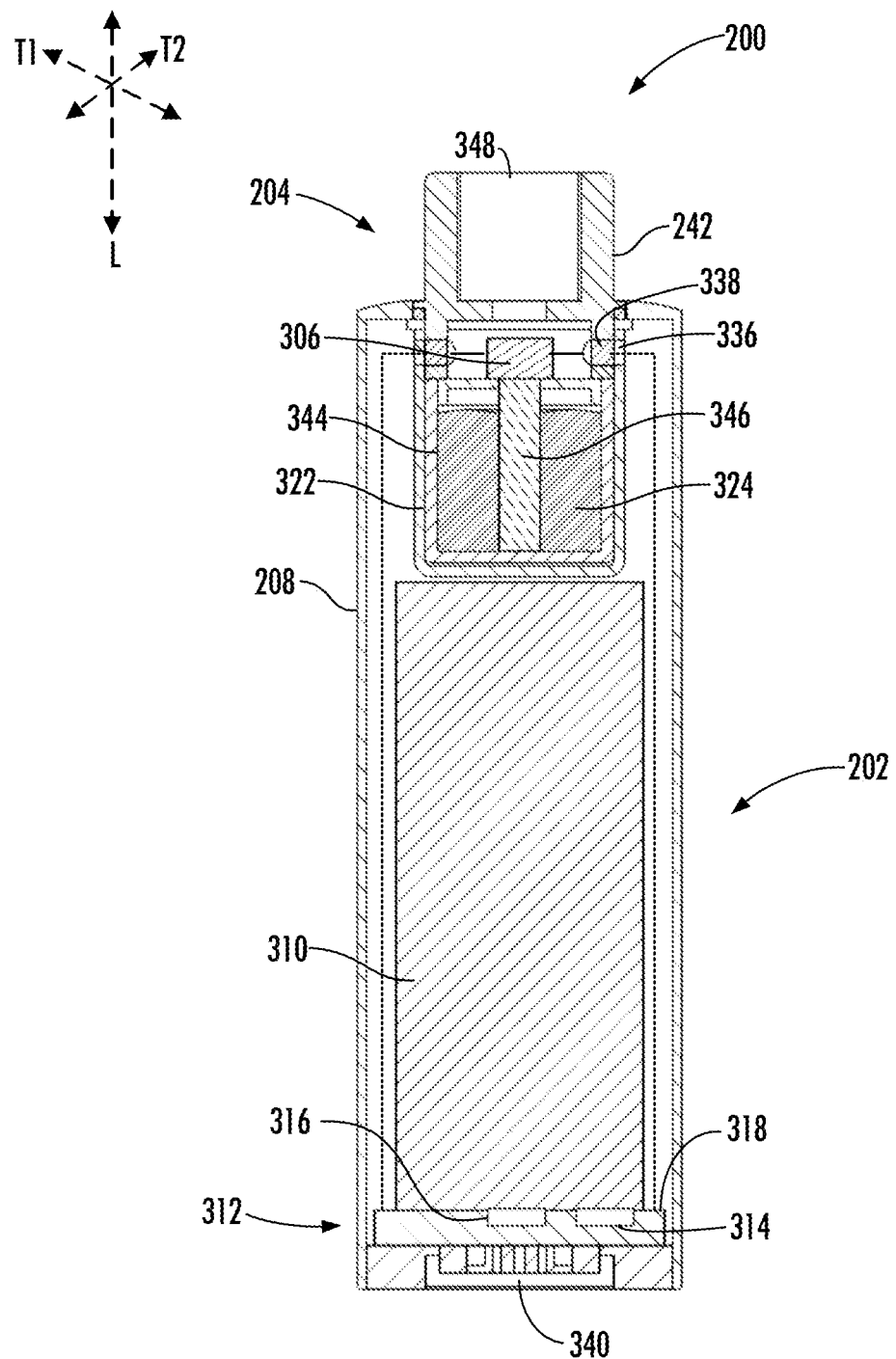
Figure 4:
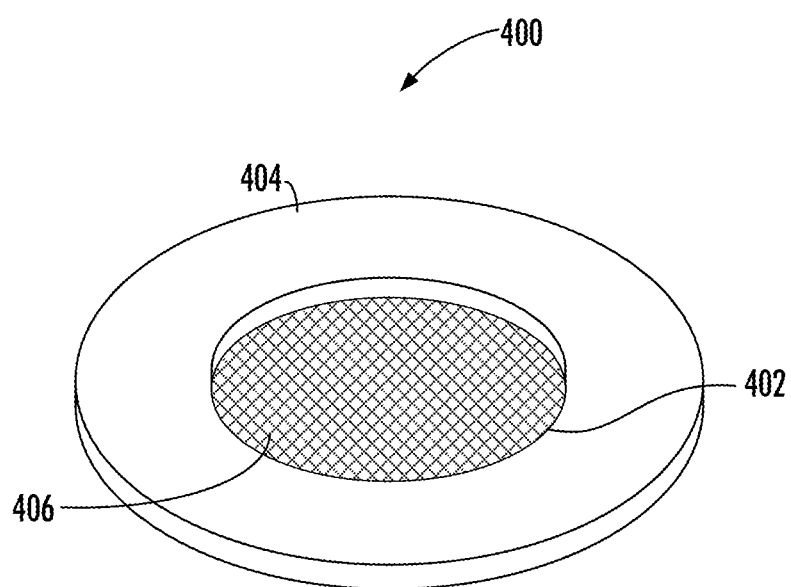
Figure 5:
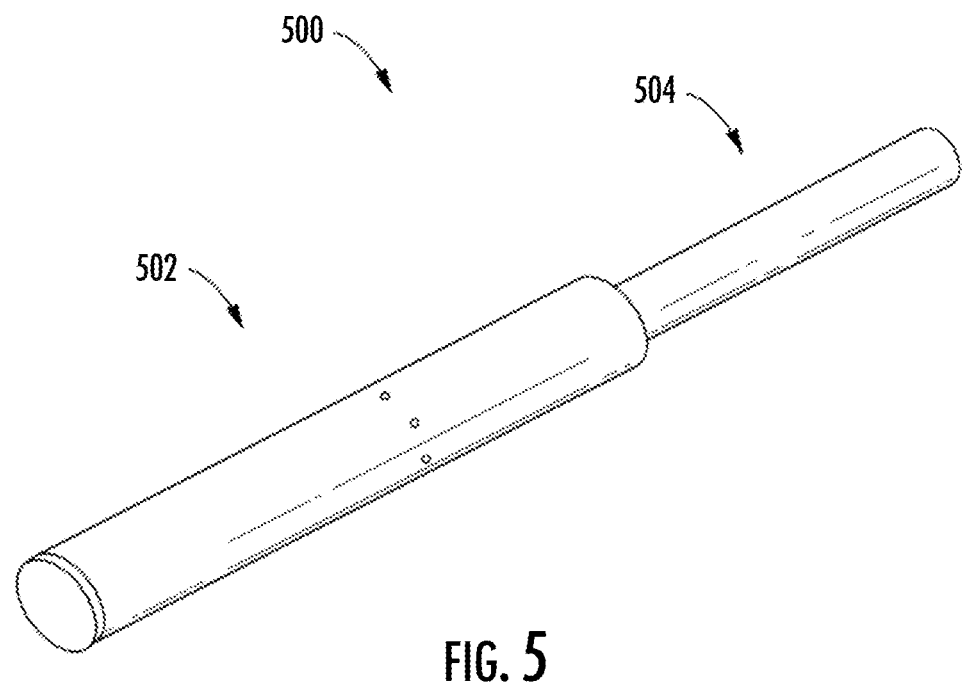
Figure 6:
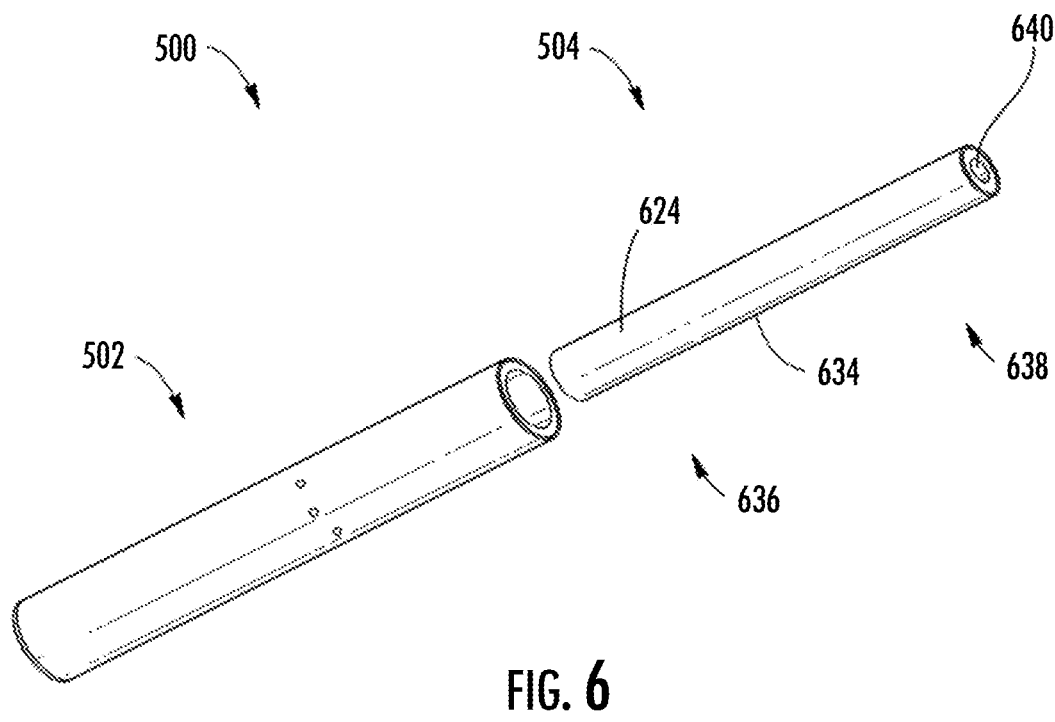
Figure 7:
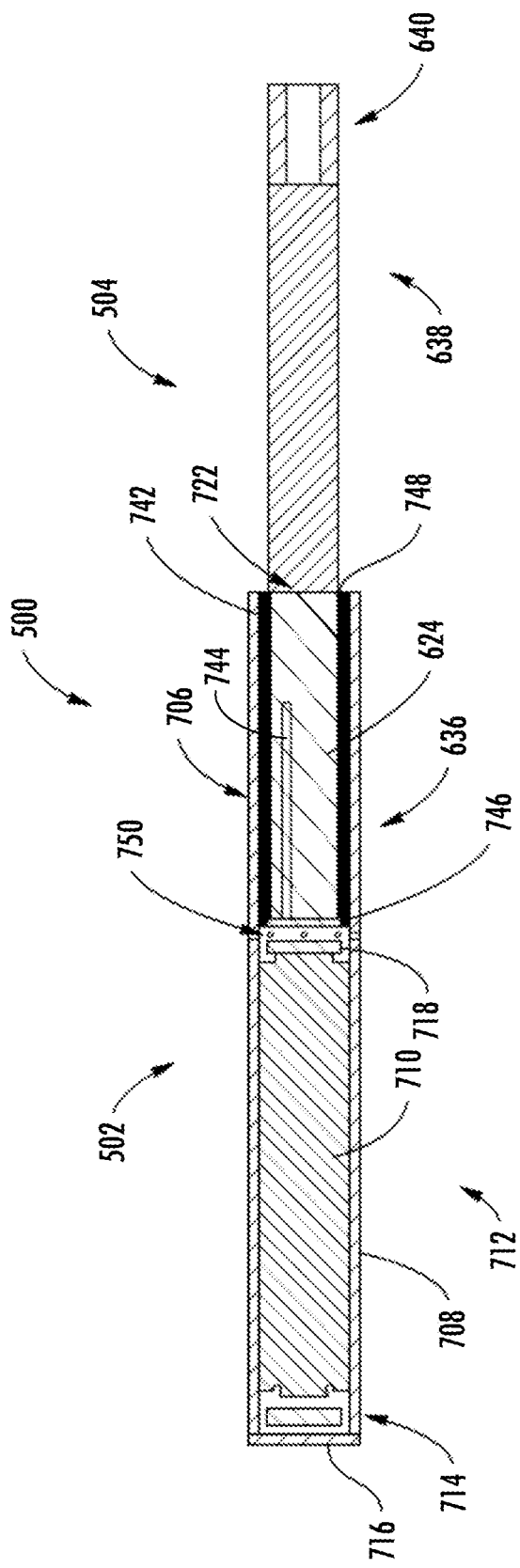
Figure 8:
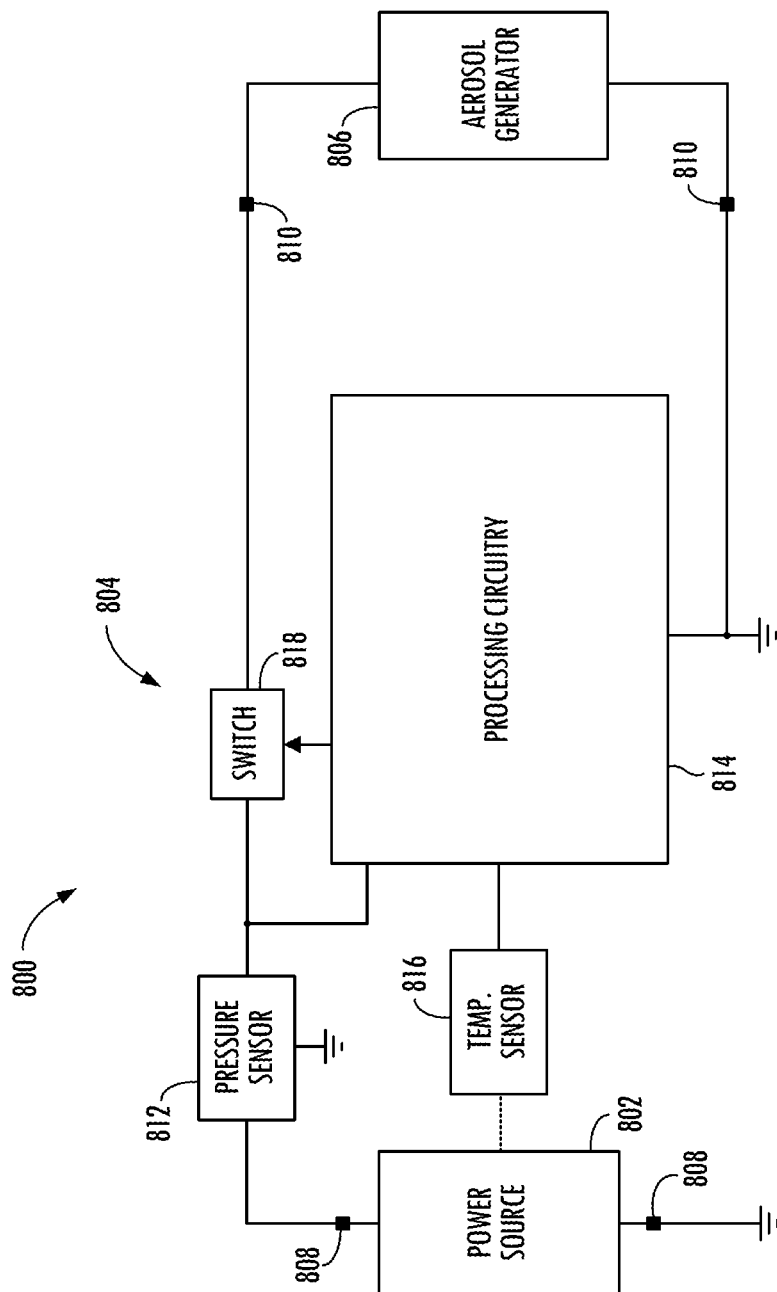
Figure 9:
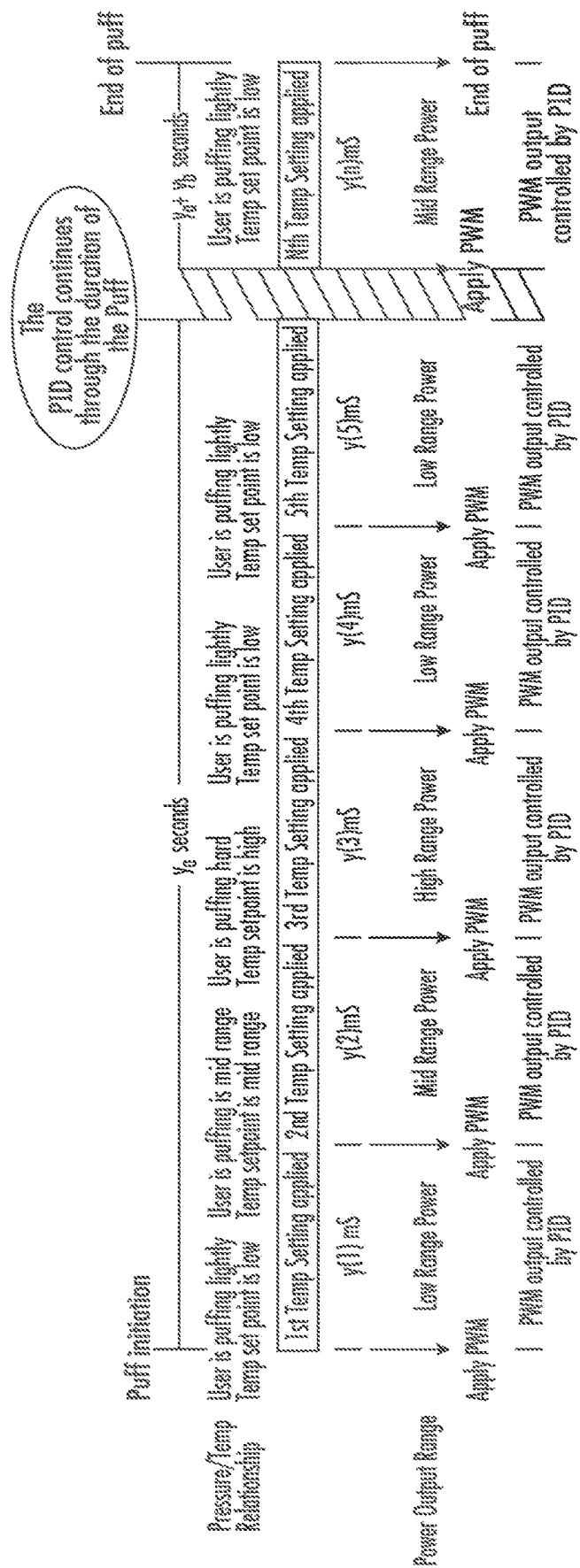

Having thus described aspects of the disclosure in the foregoing general terms, reference will now be made to the accompanying figures, which are not necessarily drawn to scale, and wherein:

FIG. 1 is a block diagram of an aerosol provision system according to some example implementations of the present disclosure;

FIGS. 2 and 3 illustrate an aerosol provision system in the form of a vapor product, according to some example implementations;

FIG. 4 illustrates a nebulizer that may be used to implement an aerosol generator of an aerosol provision system, according to some example implementations;

FIGS. 5, 6, and 7 illustrate an aerosol provision system in the form of a heat-not-burn product, according to some example implementations;

FIG. 8 is a circuit diagram of a simplified circuit of an aerosol provision system or an aerosol provision device of an aerosol provision system, according to some example implementations;

FIG. 9 illustrates an example timing diagram for adjusting the duty cycle of a modulated signal in the aerosol provision system;

FIGS. 10A, 10B, and 10C are flowcharts illustrating various operations in a method of operation of an aerosol provision device, according to various example implementations.

DETAILED DESCRIPTION

Some implementations of the present disclosure will now be described more fully hereinafter with reference to the accompanying figures, in which some, but not all implementations of the disclosure are shown. Indeed, various implementations of the disclosure may be embodied in many different forms and should not be construed as limited to the implementations set forth herein; rather, these example implementations are provided so that this disclosure will be thorough and complete, and will fully convey the scope of the disclosure to those skilled in the art. Like reference numerals refer to like elements throughout.

Unless specified otherwise or clear from context, references to first, second or the like should not be construed to imply a particular order. A feature described as being above another feature (unless specified otherwise or clear from context) may instead be below, and vice versa; and similarly, features described as being to the left of another feature else may instead be to the right, and vice versa. Also, while reference may be made herein to quantitative measures, values, geometric relationships or the like, unless otherwise stated, any one or more if not all of these may be absolute or approximate to account for acceptable variations that may occur, such as those due to engineering tolerances or the like.

As used herein, unless specified otherwise or clear from context, the "or" of a set of operands is the "inclusive or" and thereby true if and only if one or more of the operands is true, as opposed to the "exclusive or" which is false when all of the operands are true. Thus, for example, "[A] or [B]" is true if [A] is true, or if [B] is true, or if both [A] and [B] are true. Further, the articles "a" and "an" mean "one or more," unless specified otherwise or clear from context to be directed to a singular form. Furthermore, it should be understood that unless otherwise specified, the terms "data," "content," "digital content," "information," and similar terms may be at times used interchangeably.

Example implementations of the present disclosure are generally directed to delivery systems designed to deliver at least one substance to a user, such as to satisfy a particular "consumer moment." The substance may include constituents that impart a physiological effect on the user, a sensorial effect on the user, or both.

Delivery systems may take many forms. Examples of suitable delivery systems include aerosol provision systems such as powered aerosol provision systems designed to release one or more substances or compounds from an aerosol-generating material without combusting the aerosol-generating material. These aerosol provision systems may at times be referred to as non-combustible aerosol provision systems, aerosol delivery devices or the like, and the aerosol-generating material may be, for example, in the form of a solid, semi-solid, liquid or gel and may or may not contain nicotine.

Examples of suitable aerosol provision systems include vapor products, heat-not-burn products, hybrid products and the like. Vapor products are commonly known as "electronic cigarettes," "e-cigarettes" or electronic nicotine delivery systems (ENDS), although the aerosol-generating material need not include nicotine. Many vapor products are designed to heat a liquid material to generate an aerosol. Other vapor products are designed to break up an aerosol-generating material into an aerosol without heating, or with only secondary heating. Heat-not-burn products include tobacco heating products (THPs) and carbon-tipped tobacco heating products (CTHPs), and many are designed to heat a solid material to generate an aerosol without combusting the material.

Hybrid products use a combination of aerosol-generating materials, one or a plurality of which may be heated. Each of the aerosol-generating materials may be, for example, in the form of a solid, semi-solid, liquid, or gel. Some hybrid products are similar to vapor products except that the aerosol generated from a liquid or gel aerosol-generating material passes through a second material (such as tobacco) to pick up additional constituents before reaching the user. In some example implementations, the hybrid system includes a liquid or gel aerosol-generating material, and a solid aerosol-generating material. The solid aerosol-generating material may include, for example, tobacco or a non-tobacco product.

FIG. 1 is a block diagram of an aerosol provision system 100 according to some example implementations. In various examples, the aerosol provision system may be a vapor product, heat-not-burn product or hybrid product. The aerosol provision system includes one or more of each of a number of components including, for example, an aerosol provision device 102, and a consumable 104 (sometimes referred to as an article) for use with the aerosol provision device. The aerosol provision system also includes an aerosol generator 106. In various implementations, the aerosol generator may be part of the aerosol provision device or the consumable. In other implementations, the aerosol generator may be separate from the aerosol provision device and the consumable, and removably engaged with the aerosol provision device and/or the consumable.

In various examples, the aerosol provision system 100 and its components including the aerosol provision device 102 and the consumable 104 may be reusable or single-use. In some examples, the aerosol provision system including both the aerosol provision device and the consumable may be single use. In some examples, the aerosol provision device may be reusable, and the consumable may be reusable (e.g., refillable) or single use (e.g., replaceable). In yet further examples, the consumable may be both refillable and also replaceable. In examples in which the aerosol generator 106 is part of the aerosol provision device or the consumable, the aerosol generator may be reusable or single-use in the same manner as the aerosol provision device or the consumable.

In some example implementations, the aerosol provision device 102 may include a housing 108 with a power source 110 and circuitry 112. The power source is configured to provide a source of power to the aerosol provision device and thereby the aerosol provision system 100. The power source may be or include, for example, an electric power source such as a non-rechargeable battery or a rechargeable battery, solid-state battery (SSB), lithium-ion battery, supercapacitor, or the like.

The circuitry 112 may be configured to enable one or more functionalities (at times referred to as services) of the aerosol provision device 102 and thereby the aerosol provision system 100. The circuitry includes electronic components, and in some examples one or more of the electronic components may be formed as a circuit board such as a printed circuit board (PCB).

In some examples, the circuitry 112 includes at least one switch 114 that may be directly or indirectly manipulated by a user to activate the aerosol provision device 102 and thereby the aerosol provision system 100. The switch may be or include a pushbutton, touch-sensitive surface or the like that may be operated manually by a user. Additionally or alternatively, the switch may be or include a sensor configured to sense one or more process variables that indicate use of the aerosol provision device or aerosol provision system. One example is a flow sensor, pressure sensor, pressure switch or the like that is configured to detect airflow or a change in pressure caused by airflow when a user draws on the consumable 104.

The switch 114 may provide user interface functionality. In some examples, the circuitry 112 may include a user interface (UI) 116 that is separate from or that is or includes the switch. The UI may include one or more input devices and/or output devices to enable interaction between the user and the aerosol provision device 102. As described above with respect to the switch, examples of suitable input devices include pushbuttons, touch-sensitive surfaces and the like. The one or more output devices generally include devices configured to provide information in a human-perceptible form that may be visual, audible or tactile/haptic. Examples of suitable output devices include light sources such as light-emitting diodes (LEDs), quantum dot-based LEDs and the like. Other examples of suitable output devices include display devices (e.g., electronic visual displays), touchscreens (integrated touch-sensitive surface and display device), loudspeakers, vibration motors and the like.

In some examples, the circuitry 112 includes processing circuitry 118 configured to perform data processing, application execution, or other processing, control or management services according to one or more example implementations. The processing circuitry may include a processor embodied in a variety of forms such as at least one processor core, microprocessor, coprocessor, controller, microcontroller or various other computing or processing devices including one or more integrated circuits such as, for example, an ASIC (application specific integrated circuit), an FPGA (field programmable gate array), some combination thereof, or the like. In some examples, the processing circuitry may include memory coupled to or integrated with the processor, and which may store data, computer program instructions executable by the processor, some combination thereof, or the like.

As also shown, in some examples, the housing 108 and thereby the aerosol provision device 102 may also include a coupler 120 and/or a receptacle 122 structured to engage and hold the consumable 104, and thereby couple the aerosol provision device with the consumable. The coupler may be or include a connector, fastener or the like that is configured to connect with a corresponding coupler of the consumable, such as by a press fit (or interference fit) connection, threaded connection, magnetic connection or the like. The receptacle may be or include a reservoir, tank, container, cavity, receiving chamber or the like that is structured to receive and contain the consumable or at least a portion of the consumable.

The consumable 104 is an article including aerosol-generating material 124 (also referred to as an aerosol precursor composition), part or all of which is intended to be consumed during use by a user. The aerosol provision system 100 may include one or more consumables, and each consumable may include one or more aerosol-generating materials. In some examples in which the aerosol provision system is a hybrid product, the aerosol provision system may include a liquid or gel aerosol-generating material to generate an aerosol, which may then pass through a second, solid aerosol-generating material to pick up additional constituents before reaching the user. These aerosol-generating materials may be within a single consumable or respective consumables that may be separately removable.

The aerosol-generating material 124 is capable of generating aerosol, for example when heated, irradiated or energized in any other way. The aerosol-generating material may be, for example, in the form of a solid, semi-solid, liquid or gel. The aerosol-generating material may include an "amorphous solid," which may be alternatively referred to as a "monolithic solid" (i.e., non-fibrous). In some examples, the amorphous solid may be a dried gel. The amorphous solid is a solid material that may retain some fluid, such as liquid, within it. In some examples, the aerosol-generating material may include from about 50 wt %, 60 wt % or 70 wt % of amorphous solid, to about 90 wt %, 95 wt % or 100 wt % of amorphous solid.

The aerosol-generating material 124 may include one or more of each of a number of constituents such as an active substance 126, flavorant 128, aerosol-former material 130 or other functional material 132.

The active substance 126 may be a physiologically active material, which is a material intended to achieve or enhance a physiological response such as improved alertness, improved focus, increased energy, increased stamina, increased calm or improved sleep. The active substance may for example be selected from nutraceuticals, nootropics, psychoactives. The active substance may be naturally occurring or synthetically obtained. The active substance may include, for example, nicotine, caffeine, GABA (γ-aminobutyric acid), L-theanine, taurine, theine, vitamins such as B6 or B12 (cobalamin) or C, melatonin, cannabinoids, terpenes, or constituents, derivatives, or combinations thereof. The active substance may include one or more constituents, derivatives or extracts of tobacco, cannabis or another botanical.

In some examples in which the active substance 126 includes derivatives or extracts, the active substance may be or include one or more cannabinoids or terpenes.

As noted herein, the active substance 126 may include or be derived from one or more botanicals or constituents, derivatives or extracts thereof. As used herein, the term "botanical" includes any material derived from plants including, but not limited to, extracts, leaves, bark, fibers, stems, roots, seeds, flowers, fruits, pollen, husk, shells or the like. Alternatively, the material may include an active compound naturally existing in a botanical, obtained synthetically. The material may be in the form of liquid, gas, solid, powder, dust, crushed particles, granules, pellets, shreds, strips, sheets, or the like. Example botanicals are tobacco, eucalyptus, star anise, hemp, cocoa, cannabis, fennel, lemongrass, peppermint, spearmint, rooibos, chamomile, flax, ginger, *Ginkgo biloba*, hazel, hibiscus, laurel, licorice (liquorice), matcha, mate, orange skin, papaya, rose, sage, tea such as green tea or black tea, thyme, clove, cinnamon, coffee, aniseed (anise), basil, bay leaves, cardamom, coriander, cumin, nutmeg, oregano, paprika, rosemary, saffron, lavender, lemon peel, mint, juniper, elderflower, vanilla, wintergreen, beefsteak plant, curcuma, turmeric, sandalwood, cilantro, bergamot, orange blossom, myrtle, cassis, valerian, pimento, mace, damien, marjoram, olive, lemon balm, lemon basil, chive, carvi, verbena, tarragon, geranium, mulberry, ginseng, theanine, theacrine, maca, ashwagandha, damiana, guarana, chlorophyll, baobab or any combination thereof. The mint may be chosen from the following mint varieties: *Mentha Arventis, Mentha* c.v., *Mentha niliaca, Mentha piperita, Mentha piperita citrata* c.v., *Mentha piperita* c.v, *Mentha spicata crispa, Mentha cardifolia, Mentha longifolia, Mentha suaveolens variegata, Mentha pulegium, Mentha spicata* c.v. and *Mentha suaveolens.*

In yet other examples, the active substance 126 may be or include one or more of 5-hydroxytryptophan (5-HTP)/oxitriptan/Griffonia simplicifolia, acetylcholine, arachidonic acid (AA, omega-6), ashwagandha (*Withania somnifera*), Bacopa monniera, beta alanine, beta-hydroxy-beta-methylbutyrate (HMB), Centella asiatica, chai-hu, cinnamon, citicoline, cotinine, creatine, curcumin, docosahexaenoic acid (DHA, omega-3), dopamine, Dorstenia arifolia, Dorstenia Odorata, essential oils, GABA, Galphimia glauca, glutamic acid, hops, kaempferia parviflora (Thai ginseng), kava, L-carnitine, L-arginine, lavender oil, L-choline, liquorice, L-lysine, L-theanine, L-tryptophan, lutein, magnesium, magnesium L-threonate, myo-inositol, nardostachys chinensis, nitrate, oil-based extract of Viola odorata, oxygen, phenylalanine, phosphatidylserine, quercetin, resveratrol, Rhizoma gastrodiae, Rhodiola, Rhodiola rosea, rose essential oil, S-adenosylmethionine (SAMe), sceletium tortuosum, schisandra, selenium, serotonin, skullcap, spearmint extract, spikenard, theobromine, tumaric, Turnera aphrodisiaca, tyrosine, vitamin A, vitamin B3, or yerba mate.

In some example implementations, the aerosol-generating material 124 includes a flavorant 128. As used herein, the terms "flavorant" and "flavor" refer to materials which, where local regulations permit, may be used to create a desired taste, aroma or other somatosensorial sensation in a product for adult consumers. Flavorants may include naturally occurring flavor materials, botanicals, extracts of botanicals, synthetically obtained materials, or combinations thereof (e.g., tobacco, cannabis, licorice (liquorice), hydrangea, eugenol, Japanese white bark magnolia leaf, chamomile, fenugreek, clove, maple, matcha, menthol, Japanese mint, aniseed (anise), cinnamon, turmeric, Indian spices, Asian spices, herb, wintergreen, cherry, berry, redberry, cranberry, peach, apple, orange, mango, clementine, lemon, lime, tropical fruit, papaya, rhubarb, grape, durian, dragon fruit, cucumber, blueberry, mulberry, citrus fruits, Drambuie, bourbon, scotch, whiskey, gin, tequila, rum, spearmint, peppermint, lavender, aloe vera, cardamom, celery, cascarilla, nutmeg, sandalwood, bergamot, geranium, khat, naswar, betel, shisha, pine, honey essence, rose oil, vanilla, lemon oil, orange oil, orange blossom, cherry blossom, cassia, caraway, cognac, jasmine, ylang-ylang, sage, fennel, wasabi, piment, ginger, coriander, coffee, hemp, a mint oil from any species of the genus *Mentha*, eucalyptus, star anise, cocoa, lemongrass, rooibos, flax, *Ginkgo biloba*, hazel, hibiscus, laurel, mate, orange skin, rose, tea such as green tea or black tea, thyme, juniper, elderflower, basil, bay leaves, cumin, oregano, paprika, rosemary, saffron, lemon peel, mint, beefsteak plant, curcuma, cilantro, myrtle, cassis, valerian, pimento, mace, damien, marjoram, olive, lemon balm, lemon basil, chive, carvi, verbena, tarragon, limonene, thymol, camphene), flavor enhancers, bitterness receptor site blockers, sensorial receptor site activators or stimulators, sugars and/or sugar substitutes (e.g., sucralose, acesulfame potassium, aspartame, saccharine, cyclamates, lactose, sucrose, glucose, fructose, sorbitol, or mannitol), and other additives such as charcoal, chlorophyll, minerals, botanicals, or breath freshening agents. Flavorants may be imitation, synthetic or natural ingredients or blends thereof. Flavorants may be in any suitable form, for example, liquid such as an oil, solid such as a powder, or gas.

In some example implementations, the flavorant 128 may include a sensate, which is intended to achieve a somatosensorial sensation which are usually chemically induced and perceived by the stimulation of the fifth cranial nerve (trigeminal nerve), in addition to or in place of aroma or taste nerves, and these may include agents providing heating, cooling, tingling, numbing effect. A suitable heat effect agent may be, but is not limited to, vanillyl ethyl ether and a suitable cooling agent may be, but not limited to eucolyptol, WS-3.

The aerosol-former material 130 may include one or more constituents capable of forming an aerosol. In some example implementations, the aerosol-former material may include one or more of glycerine, glycerol, propylene glycol, diethylene glycol, triethylene glycol, tetraethylene glycol, 1,3-butylene glycol, erythritol, meso-Erythritol, ethyl vanillate, ethyl laurate, a diethyl suberate, triethyl citrate, triacetin, a diacetin mixture, benzyl benzoate, benzyl phenyl acetate, tributyrin, lauryl acetate, lauric acid, myristic acid, and propylene carbonate.

The one or more other functional materials 132 may include one or more of pH regulators, colouring agents, preservatives, binders, fillers, stabilizers, and/or antioxidants. Suitable binders include, for example, pectin, guar gum, fruit pectin, citrus pectin, tobacco pectin, hydroxyethyl guar gum, hydroxypropyl guar gum, hydroxyethyl locust bean gum, hydroxypropyl locust bean gum, alginate, starch, modified starch, derivatized starch, methyl cellulose, ethyl cellulose, ethylhydroxymethyl cellulose, carboxymethyl cellulose, tamarind gum, dextran, pullalon, konjac flour or xanthan gum.

In some example implementations, the aerosol-generating material 124 may be present on or in a support to form a substrate 134. The support may be or include, for example, paper, card, paperboard, cardboard, reconstituted material (e.g., a material formed from reconstituted plant material, such as reconstituted tobacco, reconstituted hemp, etc.), a plastics material, a ceramic material, a composite material, glass, a metal, or a metal alloy. In some examples, the support includes a susceptor, which may be embedded within the aerosol-generating material, or on one or either side of the aerosol-generating material.

Although not separately shown, in some example implementations, the consumable 104 may further include receptacle structured to engage and hold the aerosol-generating material 124, or substrate 134 with the aerosol-generating material. The receptacle may be or include a reservoir, tank, container, cavity, receiving chamber or the like that is structured to receive and contain the aerosol-generating material or the substrate. The consumable may include an aerosol-generating material transfer component (also referred to as a liquid transport element) configured to transport aerosol-generating material to the aerosol generator 106. The aerosol-generating material transfer component may be adapted to wick or otherwise transport aerosol-generating material via capillary action. In some examples, the aerosol-generating material transfer component may include a microfluidic chip, a micro pump or other suitable component to transport aerosol-generating material.

The aerosol generator 106 (also referred to as an atomizer, aerosolizer or aerosol production component) is configured to energize the aerosol-generating material 124 to generate an aerosol, or otherwise cause generation of an aerosol from the aerosol-generating material. More particularly, in some examples, the aerosol generator may be powered by the power source 110 under control of the circuitry 112 to energize the aerosol-generating material to generate an aerosol.

In some example implementations, the aerosol generator 106 is an electric heater configured to perform electric heating in which electrical energy from the power source is converted to heat energy, which the aerosol-generating material is subject to so as to release one or more volatiles from the aerosol-generating material to form an aerosol. Examples of suitable forms of electric heating include resistance (Joule) heating, induction heating, dielectric and microwave heating, radiant heating, arc heating and the like. More particular examples of suitable electric heaters include resistive heating elements such as wire coils, flat plates, prongs, micro heaters or the like.

In some example implementations, the aerosol generator 106 is configured to cause an aerosol to be generated from the aerosol-generating material without heating, or with only secondary heating. For example, the aerosol generator may be configured to subject the aerosol-generating material to one or more of increased pressure, vibration, or electrostatic energy. More particular examples of these aerosol generators include jet nebulizers, ultrasonic wave nebulizers, vibrating mesh technology (VMT) nebulizers, surface acoustic wave (SAW) nebulizers, and the like.

A jet nebulizer is configured to use compressed gas (e.g., air, oxygen) to break up aerosol-generating material 124 into an aerosol, and an ultrasonic wave nebulizer is configured to use ultrasonic waves to break up aerosol-generating material into an aerosol. A VMT nebulizer includes a mesh, and a piezo material (e.g., piezoelectric material, piezomagnetic material) that may be driven to vibrate and cause the mesh to break up aerosol-generating material into an aerosol. A SAW nebulizer is configured to use surface acoustic waves or Rayleigh waves to break up aerosol-generating material into an aerosol.

In some examples, the aerosol generator 106 may include a susceptor, or the susceptor may be part of the substrate 134. The susceptor is a material that is heatable by penetration with a varying magnetic field generated by a magnetic field generator that may be separate from or part of the aerosol generator. The susceptor may be an electrically-conductive material, so that penetration thereof with a varying magnetic field causes induction heating of the heating material. The heating material may be magnetic material, so that penetration thereof with a varying magnetic field causes magnetic hysteresis heating of the heating material. The susceptor in some examples may be both electrically-conductive and magnetic, so that the susceptor of these examples is heatable by both heating mechanisms.

Although not separately shown, either or both the aerosol provision device 102 or the consumable 104 may include an aerosol-modifying agent. The aerosol-modifying agent is a substance configured to modify the aerosol generated from the aerosol-generating material 124, such as by changing the taste, flavor, acidity or another characteristic of the aerosol. In various examples, the aerosol-modifying agent may be an additive or a sorbent. The aerosol-modifying agent may include, for example, one or more of a flavorant, colorant, water or carbon adsorbent. The aerosol-modifying agent may be a solid, semi-solid, liquid or gel. The aerosol-modifying agent may be in powder, thread or granule form. The aerosol-modifying agent may be free from filtration material. In some examples, the aerosol-modifying agent may be provided in an aerosol-modifying agent release component, that is operable to selectively release the aerosol-modifying agent.

The aerosol provision system 100 and its components including the aerosol provision device 102, consumable 104, and aerosol generator 106 may be manufactured with any of a number of different form factors, and with additional or alternative components relative to those described above.

FIGS. 2 and 3 illustrate an aerosol provision system 200 in the form of a vapor product, and that in some example implementations may correspond to the aerosol provision system 100. As shown, the aerosol provision system 200 may include an aerosol provision device 202 (also referred to as a control body or power unit) and a consumable 204 (also referred to as a cartridge or tank), which may correspond to respectively the aerosol provision device 102 and the consumable 104. The aerosol provision system and in particular the consumable may also include an aerosol generator corresponding to the aerosol generator 106, and in the form of an electric heater 306 such as a heating element like a metal wire coil configured to convert electrical energy to heat energy through resistance (Joule) heating. The aerosol provision device and the consumable can be permanently or detachably aligned in a functioning relationship. FIGS. 2 and 3 illustrate respectively a perspective view and a partially cut-away side view of the aerosol provision system in a coupled configuration.

As seen in FIG. 2 and the cut-away view illustrated in FIG. 3, the aerosol provision device 202 and consumable 204 each include a number of respective components. The components illustrated in FIG. 3 are representative of the components that may be present in an aerosol provision device and consumable and are not intended to limit the scope of components that are encompassed by the present disclosure.

The aerosol provision device 202 may include a housing 208 (sometimes referred to as an aerosol provision device shell) that may include a power source 310. The housing may also include circuitry 312 with a switch in the form of a sensor 314, a user interface including a light source 316 that may be illuminated with use of the aerosol provision system 200, and processing circuitry 318 (also referred to as a control component). The housing may also include a receptacle in the form of a consumable receiving chamber 322 structured to engage and hold the consumable 204. And the consumable may include an aerosol-generating material 324 that may correspond to aerosol-generating material 124, and that may include one or more of each of a number of constituents such as an active substance, flavorant, aerosol-former material or other functional material.

As also seen in FIG. 3, the aerosol provision device 202 may also include electrical connectors 336 positioned in the consumable receiving chamber 322 configured to electrically couple the circuitry and thereby the aerosol provision device with the consumable 204, and in particular electrical contacts 338 on the consumable. In this regard, the electrical connectors and electrical contacts may form a connection interface of the aerosol provision device and consumable. As also shown, the aerosol provision device may include an external electrical connector 340 to connect the aerosol provision device with one or more external devices.

Examples of suitable external electrical connectors include USB connectors, proprietary connectors such as Apple's Lightning connector, and the like.

In various examples, the consumable 204 includes a tank portion and a mouthpiece portion. The tank portion and the mouthpiece portion may be integrated or permanently fixed together, or the tank portion may itself define the mouthpiece portion (or vice versa). In other examples, the tank portion and the mouthpiece portion may be separate and removably engaged with one another.

The consumable 204, tank portion and/or mouthpiece portion may be separately defined in relation to a longitudinal axis (L), a first transverse axis (T1) that is perpendicular to the longitudinal axis, and a second transverse axis (T2) that is perpendicular to the longitudinal axis and is perpendicular to the first transverse axis. The consumable can be formed of a housing 242 (sometimes referred to as the consumable shell) enclosing a reservoir 344 (in the tank portion) configured to retain the aerosol-generating material 324. In some examples, the consumable may include an aerosol generator, such as electric heater 306 in the illustrated example. In some examples, the electrical connectors 336 on the aerosol provision device 202 and electrical contacts 338 on the consumable may electrically connect the electric heater with the power source 310 and/or circuitry 312 of the aerosol provision device.

As shown, in some examples, the reservoir 344 may be in fluid communication with an aerosol-generating material transfer component 346 adapted to wick or otherwise transport aerosol-generating material 324 stored in the reservoir housing to the electric heater 306. At least a portion of the aerosol-generating material transfer component may be positioned proximate (e.g., directly adjacent, adjacent, in close proximity to, or in relatively close proximity to) the electric heater. The aerosol-generating material transfer component may extend between the electric heater and the aerosol-generating material stored in the reservoir, and at least a portion of the electric heater may be located above a proximal end the reservoir. For the purposes of the present disclosure, it should be understood that the term "above" in this particular context should be interpreted as meaning toward a proximal end of the reservoir and/or the consumable 204 in direction substantially along the longitudinal axis (L). Other arrangements of the aerosol-generating material transfer component are also contemplated within the scope of the disclosure. For example, in some example implementations, the aerosol-generating material transfer component may be positioned proximate a distal end of the reservoir and/or arranged transverse to the longitudinal axis (L).

The electric heater 306 and aerosol-generating material transfer component 346 may be configured as separate elements that are fluidly connected, the electric heater and aerosol-generating material transfer component or may be configured as a combined element. For example, in some implementations an electric heater may be integrated into an aerosol-generating material transfer component. Moreover, the electric heater and the aerosol-generating material transfer component may be formed of any construction as otherwise described herein. In some examples, a valve may be positioned between the reservoir 344 and electric heater, and configured to control an amount of aerosol-generating material 324 passed or delivered from the reservoir to the electric heater.

An opening 348 may be present in the housing 242 (e.g., at the mouth end of the mouthpiece portion) to allow for egress of formed aerosol from the consumable 204.

As indicated above, the circuitry 312 of the aerosol provision device 202 may include a number of electronic components, and in some examples may be formed of a circuit board such as a PCB that supports and electrically connects the electronic components. The sensor 314 (switch) may be one of these electronic components positioned on the circuit board. In some examples, the sensor may comprise its own circuit board or other base element to which it can be attached. In some examples, a flexible circuit board may be utilized. A flexible circuit board may be configured into a variety of shapes. In some examples, a flexible circuit board may be combined with, layered onto, or form part or all of a heater substrate.

In some examples, the reservoir 344 may be a container for storing the aerosol-generating material 324. In some examples, the reservoir may be or include a fibrous reservoir with a substrate with the aerosol-generating material present on or in a support. For example, the reservoir can comprise one or more layers of nonwoven fibers substantially formed into the shape of a tube encircling the interior of the housing 242, in this example. The aerosol-generating material may be retained in the reservoir. Liquid components, for example, may be sorptively retained by the reservoir. The reservoir may be in fluid connection with the aerosol-generating material transfer component 346. The aerosol-generating material transfer component may transport the aerosol-generating material stored in the reservoir via capillary action—or via a micro pump—to the electric heater 306. As such, the electric heater is in a heating arrangement with the aerosol-generating material transfer component.

In use, when a user draws on the aerosol provision system 200, airflow is detected by the sensor 314, and the electric heater 306 is activated to energize the aerosol-generating material 324 to generate an aerosol. Drawing upon the mouth end of the aerosol provision system causes ambient air to enter and pass through the aerosol provision system. In the consumable 204, the drawn air combines with the aerosol that is whisked, aspirated or otherwise drawn away from the electric heater and out the opening 348 in the mouth end of the aerosol provision system.

Again, as shown in FIGS. 2 and 3, the aerosol generator of the aerosol provision system 200 is an electric heater 306 designed to heat the aerosol-generating material 324 to generate an aerosol. In other implementations, the aerosol generator is designed to break up the aerosol-generating material without heating, or with only secondary heating. FIG. 4 illustrates a nebulizer 400 that may be used to implement the aerosol generator of an aerosol provision system, according to some these other example implementations.

As shown in FIG. 4, the nebulizer 400 includes a mesh plate 402 and a piezo material 404 that may be affixed to one another. The piezo material may be driven to vibrate and cause the mesh plate to break up aerosol-generating material into an aerosol. In some examples, the nebulizer may also include a supporting component located on a side of the mesh plate opposite the piezo material to increase the longevity of the mesh plate, and/or an auxiliary component between the mesh plate and the piezo material to facilitate interfacial contact between the mesh plate and the piezo material.

In various example implementations, the mesh plate 402 may have a variety of different configurations. The mesh plate may have a flat profile, a domed shape (concave or convex with respect to the aerosol-generating material), or a flat portion and a domed portion. The mesh plate defines a plurality of perforations 406 that may be substantially uniform or vary in size across a perforated portion of the mesh plate. The perforations may be circular openings or non-circular openings (e.g., oval, rectangular, triangular, regular polygon, irregular polygon). In three-dimensions, the perforations may have a fixed cross section such as in the case of cylindrical perforations with a fixed circular cross section, or a variable cross section such as in the case of truncated cone perforations with a variable circular cross section. In other implementations, the perforations may be tetragonal or pyramidal.

The piezo material 404 may be or include a piezoelectric material or a piezomagnetic material. A piezoelectric material may be coupled to circuitry configured to produce an oscillating electric signal to drive the piezoelectric material to vibrate. For a piezomagnetic material, the circuitry may produce a pair of antiphase, oscillating electric signals to drive a pair of magnets to produce antiphase, oscillating magnetic fields that drives the piezomagnetic material to vibrate.

The piezo material 404 may be affixed to the mesh plate 402, and vibration of the piezo material may in turn cause the mesh plate to vibrate. The mesh plate may be in contact with or immersed in aerosol-generating material, in sufficient proximity of aerosol-generating material, or may otherwise receive aerosol-generating material via an aerosol-generating material transfer component. The vibration of the mesh plate, then, may cause the aerosol-generating material to pass through the perforations 406 that break up the aerosol-generating material into an aerosol. More particularly, in some examples, aerosol-generating material may be driven through the perforations 406 in the vibrating mesh plate 402 resulting in aerosol particles. In other examples in which the mesh plate is in contact with or immersed in aerosol-generating material, the vibrating mesh plate may create ultrasonic waves within aerosol-generating material that cause formation of an aerosol at the surface of the aerosol-generating material.

As described above, hybrid products use a combination of aerosol-generating materials, and some hybrid products are similar to vapor products except that the aerosol generated from one aerosol-generating material may pass through a second aerosol-generating material to pick up additional constituents. Another similar aerosol provision system in the form of a hybrid product may therefore be constructed similar to the vapor product in FIGS. 2 and 3 (with an electric heater 306 or a nebulizer 400). The hybrid product may include a second aerosol-generating material through which aerosol from the aerosol-generating material 324 is passed to pick up additional constituents before passing through the opening 348 in the mouth end of the aerosol provision system.

FIGS. 5, 6 and 7 illustrate an aerosol provision system 500 in the form of a heat-not-burn product, and that in some example implementations may correspond to the aerosol provision system 100. As shown, the aerosol provision system may include an aerosol provision device 502 (also referred to as a control body or power unit) and a consumable 504 (also referred to as an aerosol source member), which may correspond to respectively the aerosol provision device 102 and the consumable 104. The aerosol provision system and in particular the aerosol provision device may also include an aerosol generator corresponding to the aerosol generator 106, and in the form of an electric heater 706. The aerosol provision device and the consumable can be permanently or detachably aligned in a functioning relationship. FIG. 5 illustrates the aerosol provision system in a coupled configuration, whereas FIG. 6 illustrates the aerosol provision system in a decoupled configuration. FIG. 7 illustrates a partially cut-away side view of the aerosol provision system in the coupled configuration.

As seen in FIGS. 5, 6 and 7, the aerosol provision device 502 and consumable 504 each include a number of respective components. The components illustrated in the figures are representative of the components that may be present in an aerosol provision device and consumable and are not intended to limit the scope of components that are encompassed by the present disclosure.

The aerosol provision device 502 may include a housing 708 (sometimes referred to as an aerosol provision device shell) that may include a power source 710. The housing may also include circuitry 712 with a switch in the form of a sensor 714, a user interface including a light source 716 that may be illuminated with use of the aerosol provision system 500, and processing circuitry 718 (also referred to as a control component). In some examples, at least some of the electronic components of the circuitry may be formed of a circuit board or a flexible circuit board that supports and electrically connects the electronic components.

The housing 708 may also include a receptacle in the form of a consumable receiving chamber 722 structured to engage and hold the consumable 504. The consumable may include an aerosol-generating material 624 that may correspond to aerosol-generating material 124, and that may include one or more of each of a number of constituents such as an active substance, flavorant, aerosol-former material or other functional material. And the aerosol-generating material may be present on or in a support to form a substrate 634.

In the coupled configuration of the aerosol provision system 500, the consumable 504 may be held in the receiving chamber 722 in varying degrees. In some examples, less than half or approximately half of the consumable may be held in the receiving chamber. In other examples, more than half of the consumable may be held in the receiving chamber. In yet other examples, substantially the entire consumable may be held in the receiving chamber.

As shown in FIGS. 6 and 7, in various implementations of the present disclosure, the consumable 504 may include a heated end 636 sized and shaped for insertion into the aerosol provision device 502, and a mouth end 638 upon which a user draws to create the aerosol. In various implementations, at least a portion of the heated end may include the aerosol-generating material 624.

In some example implementations, the mouth end 608 of the consumable 504 may include a filter 640 made of a material such as cellulose acetate or polypropylene. The filter may additionally or alternatively contain strands of tobacco containing material. In some examples, at least a portion of the consumable may be wrapped in an exterior overwrap material, which may be formed of any material useful to provide additional structure, support and/or thermal resistance. In some examples, an excess length of the overwrap at the mouth end of the consumable may function to simply separate the aerosol-generating material 624 from the mouth of a user or to provide space for positioning of a filter material, or to affect draw on the consumable or to affect flow characteristics of the aerosol leaving the consumable during draw.

The electric heater 706 may perform electric heating of the aerosol-generating material 624 by resistance (Joule) heating, induction heating, dielectric and microwave heating, radiant heating, arc heating and the like. The electric heater may have a variety of different configurations. In some examples, at least a portion of the electric heater may surround or at least partially surround at least a portion of the consumable 504 including the aerosol-generating material when inserted in the aerosol provision device 502. In other examples, at least a portion of the electric heater may penetrate the consumable when the consumable is inserted into the aerosol provision device. In some examples, the substrate 634 material may include a susceptor, which may be embedded within the aerosol-generating material, or on one or either side of the aerosol-generating material.

Although shown as a part of the aerosol provision device 502, the electric heater 706 may instead be a part of the consumable 504. In some examples, the electric heater or a part of the electric heater may be may be combined, packaged or integral with (e.g., embedded within) the aerosol-generating material 624.

As shown, in some examples, the electric heater 706 may extend proximate an engagement end of the housing 708, and may be configured to substantially surround a portion of the heated end 636 of the consumable 504 that includes the aerosol-generating material 624. The electric heater 706 may be or may include an outer cylinder 742, and one or more resistive heating elements 744 such as prongs surrounded by the outer cylinder to create the receiving chamber 722, which may extend from a receiving base 746 of the aerosol provision device to an opening 748 of the housing 708 of the aerosol provision device. In some examples, the outer cylinder may be a double-walled vacuum tube constructed of stainless steel so as to maintain heat generated by the resistive heating element(s) within the outer cylinder, and more particularly, maintain heat generated by the resistive heating element(s) within the aerosol-generating material.

Like the electric heater 706, the resistive heating element(s) 744 may have a variety of different configurations, and vary in number from one resistive heating element to a plurality of resistive heating elements. As shown, the resistive heating element(s) may extend from a receiving base 746 of the aerosol provision device 502. In some examples, the resistive heating element(s) may be located at or around an approximate radial center of the heated end 636 of the consumable 504 when inserted into the aerosol provision device. In some examples, the resistive heating element(s) may penetrate into the heated end of the consumable and in direct contact with the aerosol-generating material. In other examples, the resistive heating element(s) may be located inside (but out of direct contact with) a cavity defined by an inner surface of the heated end of the consumable.

In some examples, the resistive heating element(s) 744 of the electric heater 706 may be connected in an electrical circuit that includes the power source 710 such that electric current produced by the power source may pass through the resistive heating element(s). The passage of the electric current through the resistive heating element(s) may in turn cause the resistive heating element(s) to produce heat through resistance (Joule) heating.

In other examples, the electric heater 706 including the outer cylinder 742 and the resistive heating element(s) 744 may be configured to perform induction heating in which the outer cylinder may be connected in an electrical circuit that includes the power source 710, and the resistive heating element(s) may be connected in another electrical circuit. In this configuration, the outer cylinder and resistive heating element(s) may function as a transformer in which the outer cylinder is an induction transmitter, and the resistive heating element(s) is/are an induction receiver. In some of these examples, the outer cylinder and the resistive heating element(s) may parts of the aerosol provision device 502. In other of these examples, the outer cylinder may be a part of the aerosol provision device, and the resistive heating element(s) may be a part of the consumable 504.

The outer cylinder 730 may be provided an alternating current directly from the power source 710, or indirectly from the power source in which an inverter (as part of the circuitry 712) is configured to convert direct current from the power source to an alternating current. The alternating current drives the outer cylinder to generate an oscillating magnetic field, which induces eddy currents in the resistive heating element(s) 744. The eddy currents in turn cause the resistive heating element(s) to generate heat through resistance (Joule) heating. In these examples, the resistive heating element(s) may be wirelessly heated to form an aerosol from the aerosol-generating material 624 positioned in proximity to the resistive heating element(s).

In various example implementations, the aerosol provision device 502 may include an air intake 750 (e.g., one or more openings or apertures) in the housing 708 (and perhaps also the receiving base 746) to enable airflow into the receiving chamber 722. When a use draws on the mouth end 638 of the consumable 504, the airflow may be drawn through the air intake into the receiving chamber, pass into the consumable, and drawn through the aerosol-generating material 624. The airflow may be detected by the sensor 714, and the electric heater 706 may be activated to energize the aerosol-generating material to generate an aerosol. The airflow may combine with the aerosol that is whisked, aspirated or otherwise drawn out an opening at the mouth end of the aerosol provision system. In examples including the filter 640, the airflow combined with the aerosol may be drawn out an opening of the filter at the mouth end.

As described above, an aerosol provision system may include an aerosol provision device and an aerosol generator. The aerosol provision device may include a power source and circuitry, and the circuitry may include various electronic components. FIG. 8 illustrates a circuit diagram of a simplified circuit 800 of an aerosol provision system or an aerosol provision device of an aerosol provision system, according to some example implementations of the present disclosure. Examples of suitable aerosol provision systems for which the circuit is suitable include aerosol provision system 100, 200, 500; and examples of suitable aerosol provision devices include aerosol provision device 102, 202, 502.

As shown, the simplified circuit 800 includes a power source 802, circuitry 804 and an aerosol generator 806 that may correspond to respective ones of the power source 110, circuitry 112 and aerosol generator 106. In more specific examples, the power source 802 may correspond to power source 310, 710, and the circuitry 804 may correspond to circuitry 312, 712. Also in more specific examples, the aerosol generator 806 may correspond to electric heater 306, nebulizer 400, or electric heater 706. The aerosol generator 806 may be powered by the power source 802 under control of the circuitry 804 to energize aerosol-generating material (e.g., aerosol-generating material 124, 324, 624) to generate an aerosol for delivery to a user.

As shown in FIG. 8, the circuit 800 may include terminals 808 to connect the power source 802 circuitry 804, and/or second terminals 810 to connect the aerosol generator to the circuitry.

The circuitry 804 may include electronic components such as a pressure sensor 812 that may correspond to switch 114, 314, 714, and processing circuitry 814 that may correspond to processing circuitry 118, 318, 718. The circuitry may also include a temperature sensor 816, and a high-side load switch 818. Examples of suitable temperature sensors include a resistance temperature detector (RTD), a thermistor, and the like. In examples in which the aerosol generator is or includes an electric heater (e.g., electric heater 306, 706), the electric heater may also be used to produce measurements of temperature. For example, the resistance of the electric heater may change proportionally with the temperature of the electric heater as it is powered. This change in resistance may be measureable and thus may also be used to produce measurements of temperature.

The high-side load switch 818 may be coupled to or coupleable with the aerosol generator 806. In some examples in which the aerosol generator is part of the aerosol provision device, the high-side load switch may be coupled to the aerosol generator. In other examples in which the aerosol generator is separate from the aerosol provision device, the high-side load switch may be coupleable with the aerosol generator, such as via the second terminals 810.

According to some example implementations, the pressure sensor 812 may be configured to produce measurements of pressure caused by airflow through the aerosol provision device, or more particularly a housing (e.g., housing 108, 208, 708) of the aerosol provision device. The temperature sensor 816 may be configured to produce measurements of temperature of one or both of the aerosol generator 806 or the aerosol-generating material.

The processing circuitry 814 may be coupled to the high-side load switch 818, the pressure sensor 812, and the temperature sensor 816. The processing circuitry may be configured to output a signal to cause the high-side load switch to switchably connect and disconnect power from the power source 804 to the aerosol generator, based on the measurements of pressure and the measurements of temperature. The processing circuitry may be configured to output the signal to power the aerosol generator 806 for an aerosol-production time period that is coextensive with a puff action. In these examples, the signal may be a modulated signal with an adjustable duty cycle (e.g., a pulse-width modulation (PWM) signal or a pulse-frequency modulation (PFM) signal).

In some examples, the processing circuitry 816 may be configured to implement a proportional-integral-derivative (PID) algorithm to adjust the duty cycle of the signal based on the measurements of pressure and the measurements of temperature according to a predetermined relationship between pressure and temperature.

In some examples, the predetermined relationship is one in which the measurements of temperature or the measurements of pressure are determined by the processing circuitry to take precedence for implementing the PID algorithm to adjust the duty cycle. For example, when the measurements of temperature are low, then the measurements of pressure may take precedence over the measurements of temperature, and the PID algorithm may be implemented to adjust the duty cycle with a longer duty cycle if the measurements of pressure are high, or with a shorter duty cycle if the measurements of pressure are low.

In other examples, when the measurements of temperature are high, then the measurements of temperature may take precedence over measurements of pressure. Accordingly, the PID algorithm may be implemented to adjust the duty cycle to ensure that a maximum temperature is not exceeded.

In yet other examples, the predetermined relationship includes utilizing a lookup table (LUT) that may be stored in memory coupled to or integrated with the processing circuitry and containing temperature values that are associated with the measurements of pressure. In these other examples, the processing circuitry may utilize the LUT while implementing the PID algorithm to adjust the duty cycle based on the temperature values that are associated with the measurements of pressure in the LUT. The LUT may be of a suitable size for storing the temperature values associated with the measurements of pressure, e.g., 256-bit, 512-bit, or the like.

In some examples, the processing circuitry 816 may be configured to implement the PID algorithm to adjust the duty cycle when the measurements of temperature are below or above a temperature target that varies with the measurements of pressure, according to the predetermined relationship between pressure and temperature. In this manner, implementation of the PID algorithm may reduce a hysteresis condition in one or both of the aerosol generator 802 or the aerosol-generating material as the duty cycle is adjusted to reach the temperature target.

In some examples, the temperature target may be a target set point temperature. In other examples, the target may be a range of temperatures. One example of a suitable range of temperatures is reflected by a target set point temperature +/− an acceptable tolerance from the target set point temperature. A suitable range of temperatures may also be used to reflect an amount of added hysteresis.

In some examples, the temperature target may vary over time in accordance with a temperature or power control profile that may be applied during a time period of usage. This may be particularly useful for heat-not-burn devices in which a solid or semi-solid aerosol precursor composition may be heated for a longer duration than a liquid aerosol precursor composition in an electronic cigarette. In particular, in a heat-not-burn device, a higher temperature may be applied during an initial period as the aerosol precursor composition is prepared to for inhalation, and then lowered after a period of time. For more information on examples of suitable control profiles, see U.S. Pat. No. 9,498,000 to Kuczaj, which is incorporated herein by reference.

In some examples, the temperature target may vary or otherwise be variable according to the measurement of pressure. In more particular examples, the target may be variable according to a predetermined relationship between pressure and the temperature target.

In some examples, the measurements of temperature may include initial measurements of temperature produced after an initial puff action. The initial measurements of temperature may be below an initial temperature target that is less than the temperature target. The processing circuitry 816 may be configured to output the signal with a longer duty cycle to pre-heat the aerosol-generating material or the aerosol generator 802 to the initial temperature target. In this manner, the pre-heat may be achieved by outputting the signal with the longer duty cycle based on the initial measurements of temperature and to reach the initial temperature target, and outputting the signal with the longer duty cycle includes implementing the PID algorithm to ensure that the initial temperature target is not exceeded.

FIG. 9 illustrates an example of a timing diagram adjusting the duty cycle of a modulated signal in the aerosol provision system. In this example, the sub-intervals show examples of duty cycles applied for y(n) milliseconds (ms) under varying conditions of temperature and pressure. In some examples, the first sub-interval may correspond to a pre-heat interval. The modulated signal is adjusted by the PID algorithm and is a PWM signal in this example, but in other examples another type of modulated signal may be implemented, e.g., a PFM signal.

FIG. 10A is a flowchart illustrating various operations in a method 1000 of operating an aerosol provision system equipped with circuitry 804 including processing circuitry 814, and an aerosol generator 806 powered by a power source 802 under control of the circuitry to energize aerosol-generating material to generate an aerosol for delivery to a user, according to some example implementations of the present disclosure. The method may include producing measurements of pressure caused by airflow through the aerosol provision device, as shown at block 1002. The method may also include producing measurements of temperature of one or both of the aerosol generator or the aerosol-generating material, as shown at block 1004.

As shown at block 1006, the method 1000 may also include outputting a signal by the processing circuitry 814 to cause a high-side load switch 818 to switchably connect and disconnect power from the power source 802 to the aerosol generator 806. In this regard, the connecting and disconnecting may be based on the measurements of pressure and the measurements of temperature. The signal output by the processing circuitry may be a modulated signal with a duty cycle that is adjustable, and as shown at block 1008, the processing circuitry may implement a proportional-integral-derivative (PID) algorithm to adjust the duty cycle may be based on the measurements of pressure and the measurements of temperature according to a predetermined relationship between pressure and temperature.

In some examples, outputting the signal at block 1006 may include outputting the signal to power the aerosol generator 802 for an aerosol-production time period that is coextensive with a puff action, as shown at block 1010 of FIG. 10B.

In some examples, implementing the PID algorithm at block 1008 includes implementing the PID algorithm to adjust the duty cycle when the measurements of temperature are below or above a temperature target that varies with the measurements of pressure according to the predetermined relationship between pressure and temperature, as shown at block 1012 of FIG. 10C. Implementing the PID algorithm at block 1012 may include implementing the PID algorithm to cause the reduction of a hysteresis condition in one or both of the aerosol generator 806 or the aerosol-generating material as the duty cycle is adjusted to reach the temperature target, as shown at block 1014.

Many modifications and other implementations of the disclosure will come to mind to one skilled in the art to which this disclosure pertains having the benefit of the teachings presented in the foregoing descriptions and the associated figures. Therefore, it is to be understood that the disclosure is not to be limited to the specific implementations disclosed herein and that modifications and other implementations are intended to be included within the scope of the appended claims. Although specific terms are employed herein, they are used in a generic and descriptive sense only and not for purposes of limitation.

What is claimed is:

1. An aerosol provision device comprising:
a housing;
circuitry; and
one or more of a coupler or a receptacle structured to engage and hold a consumable including aerosol-generating material, the aerosol provision device or the consumable further including an aerosol generator powered by a power source under control of the circuitry to energize the aerosol-generating material to generate an aerosol for delivery to a user,
wherein the circuitry includes:
a pressure sensor configured to produce measurements of pressure caused by airflow through the housing;
a temperature sensor configured to produce measurements of temperature of one or both of the aerosol generator or the aerosol-generating material;
a high-side load switch coupled to or coupleable with the aerosol generator; and
processing circuitry coupled to the high-side load switch, the pressure sensor, and the temperature sensor, the processing circuitry configured to output a signal to cause the high-side load switch to switchably connect and disconnect power from the power source to the aerosol generator, based on the measurements of pressure and the measurements of temperature,
wherein the signal is a modulated signal with a duty cycle that is adjustable, and the processing circuitry is configured to implement a proportional-integral-derivative (PID) algorithm to adjust the duty cycle based on the measurements of pressure and the measurements of temperature according to a predetermined relationship between pressure and temperature, and
wherein the processing circuitry determines from the predetermined relationship whether the measurements of temperature or the measurements of pressure take precedence for implementing the PID algorithm to adjust the duty cycle.

2. The aerosol provision device of claim 1 further comprising the power source, and wherein the high-side load switch is coupled to and between the power source and the aerosol generator.

3. The aerosol provision device of claim 1, wherein the processing circuitry is configured to implement the PID algorithm to adjust the duty cycle when the measurements of temperature are below or above a temperature target that varies with the measurements of pressure according to the predetermined relationship between pressure and temperature.

4. The aerosol provision device of claim 3, wherein the processing circuitry configured to implement the PID algorithm to adjust the duty cycle when the measurements of temperature are below or above the temperature target causes the reduction of a hysteresis condition in one or both of the aerosol generator or the aerosol-generating material as the duty cycle is adjusted to reach the temperature target.

5. The aerosol provision device of claim 1, wherein the measurements of temperature include initial measurements of temperature produced after an initial puff action in which the initial measurements of temperature are below an initial temperature target that is less than the temperature target, and the processing circuitry is configured to output the signal with a longer duty cycle to pre-heat the aerosol-generating material or the aerosol generator to the initial temperature target.

6. The aerosol provision device of claim 1, wherein the modulated signal is a pulse-width modulation (PWM) signal or a pulse-frequency modulation (PFM) signal.

7. The aerosol provision device of claim 1, wherein the temperature sensor is a resistance temperature detector (RTD).

8. The aerosol provision device of claim 1, wherein the processing circuitry configured to output the signal includes the processing circuitry configured to output the signal to power the aerosol generator for an aerosol-production time period that is coextensive with a puff action.

9. A method of operating an aerosol provision system equipped with circuitry including processing circuitry, and an aerosol generator powered by a power source under control of the circuitry to energize aerosol-generating material to generate an aerosol for delivery to a user, the method comprising:

producing measurements of pressure caused by airflow through the aerosol provision device;

producing measurements of temperature of one or both of the aerosol generator or the aerosol-generating material; and outputting a signal by the processing circuitry to cause a high-side load switch to switchably connect and disconnect power from the power source to the aerosol generator, based on the measurements of pressure and the measurements of temperature, wherein the signal output by the processing circuitry is a modulated signal with a duty cycle that is adjustable, the processing circuitry implementing a proportional-integral-derivative (PID) algorithm to adjust the duty cycle based on the measurements of pressure and the measurements of temperature according to a predetermined relationship between pressure and temperature, and wherein the processing circuitry determines from the predetermined relationship whether the measurements of temperature or the measurements of pressure take precedence for implementing the PID algorithm to adjust the duty cycle.

10. The method of claim 9, wherein the aerosol provision device is further equipped with the power source, and the high-side load switch is coupled to and between the power source and the aerosol generator.

11. The method of claim 9, wherein the processing circuitry implements the PID algorithm to adjust the duty cycle when the measurements of temperature are below or above a temperature target that varies with the measurements of pressure according to the predetermined relationship between pressure and temperature.

12. The method of claim 11, wherein the processing circuitry implements the PID algorithm to adjust the duty cycle when the measurements of temperature are below or above the temperature target to cause the reduction of a hysteresis condition in one or both of the aerosol generator or the aerosol-generating material as the duty cycle is adjusted to reach the temperature target.

13. The method of claim 9, wherein the measurements of temperature include initial measurements of temperature produced after an initial puff action in which the initial measurements of temperature are below an initial temperature target that is less than the temperature target, and wherein the signal output by the processing circuitry includes a longer duty cycle to pre-heat the aerosol-generating material or the aerosol generator to the initial temperature target.

14. The method of claim 9, wherein the modulated signal is a pulse-width modulation (PWM) signal or a pulse-frequency modulation (PFM) signal.

15. The method of claim 9, wherein the temperature sensor is a resistance temperature detector (RTD).

16. The method of claim 9, wherein outputting the signal includes outputting the signal to power the aerosol generator for an aerosol-production time period that is coextensive with a puff action.

\* \* \* \* \*